United States Patent
Roncucci et al.

(10) Patent No.: US 10,730,890 B2
(45) Date of Patent: Aug. 4, 2020

(54) PHTHALOCYANINE DERIVATIVE CONSISTING OF A MIXTURE OF 4 ISOMERS

(71) Applicant: MOLTENI THERAPEUTICS S.R.L., Scanducci (IT)

(72) Inventors: Gabrio Roncucci, Poggibonsi (IT); Donata Dei, San Gimignano (IT); Giacomo Chiti, Prato (IT); Daniele Nistri, Prato (IT)

(73) Assignee: MOLTENI THERAPEUTICS S.R.L., Scanducci (FI) (IT)

( * ) Notice: Subject to any disclaimer, the term of this patent is extended or adjusted under 35 U.S.C. 154(b) by 0 days.

(21) Appl. No.: 15/008,875

(22) Filed: Jan. 28, 2016

(65) Prior Publication Data

US 2017/0073358 A1    Mar. 16, 2017

Related U.S. Application Data (62) Division of application No. 13/387,407, filed as application No. PCT/EP2010/061112 on Jul. 30, 2010, now abandoned.

(30) Foreign Application Priority Data

Jul. 30, 2009    (IT) ................ FI2009A0168

(51) Int. Cl.
  *C07D 487/22*    (2006.01)
  *C07F 3/06*      (2006.01)
  *A61K 31/409*    (2006.01)

(52) U.S. Cl.
  CPC .............. *C07F 3/06* (2013.01); *A61K 31/409* (2013.01); *C07D 487/22* (2013.01)

(58) Field of Classification Search
  CPC .................................................. C07D 487/22
  See application file for complete search history.

(56) References Cited

FOREIGN PATENT DOCUMENTS

| EP | 1 444 236 | 6/1985 |
| EP | 1 883 640 | 2/2008 |
| WO | 2006 117396 | 11/2006 |

*Primary Examiner* — Brian E McDowell
(74) *Attorney, Agent, or Firm* — Pepper Hamilton LLP (57) ABSTRACT

There is described a phthalocyanine derivative of formula (I) consisting of 4 isomers wherein the relative isomer B content is less than or equal to 1% by weight.

(I)

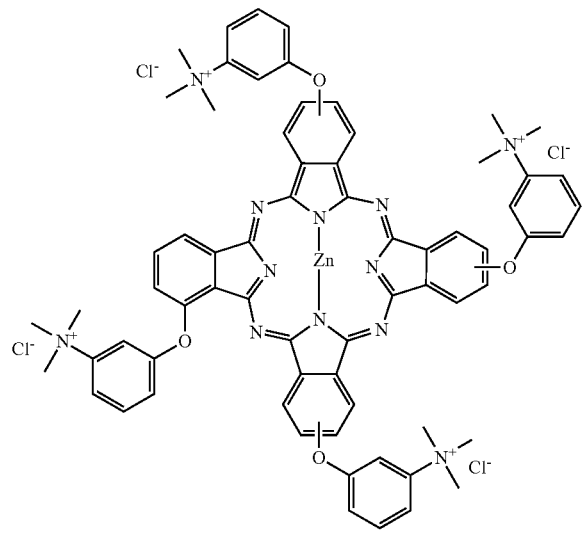

(with low isomer B content)

4 Claims, 5 Drawing Sheets

PHTHALOCYANINE DERIVATIVE CONSISTING OF A MIXTURE OF 4 ISOMERS

CROSS-REFERENCE TO RELATED APPLICATIONS

This application is a divisional of U.S. application Ser. No. 13/387,407, filed Jan. 27, 2012, which is a National Phase of PCT/EP2010/061112, filed Jul. 30, 2010, which claims priority from Italian Application No. FI 2009A000168 filed Jul. 30, 2009, disclosures of which are all incorporated by reference.

FIELD OF THE INVENTION

The invention relates to the field of photosensitising compounds for therapeutic use.

BACKGROUND ART

It is known that molecules containing the chromo/fluorophore phthalocyanine macrocycle produce reactive species of oxygen, such as radicals or singlet oxygen, by interaction with visible light.

For these properties phthalocyanine compounds have proposed in photodynamic therapy (hereinafter indicated with the initials "PDT") both for therapeutic treatment and for diagnostic purposes prior treatment.

Examples of these compounds are described by Ogura et al. *Journal of Porphyrins and Phthalocyanines* 2006, 10, 1116-1124.

Photosensitizing agents useful in PDT are Zinc phthalocyanine compounds and their conjugates described in the patent EP 906 758, by the Applicant.

Moreover, EP 1 444 236 and in EP 1 883 640 (both by the Applicant) respectively describe a process for the separation of regioisomers mixtures and a process for the preparation of chlorides of phthalocyanine compounds.

Figure 1:
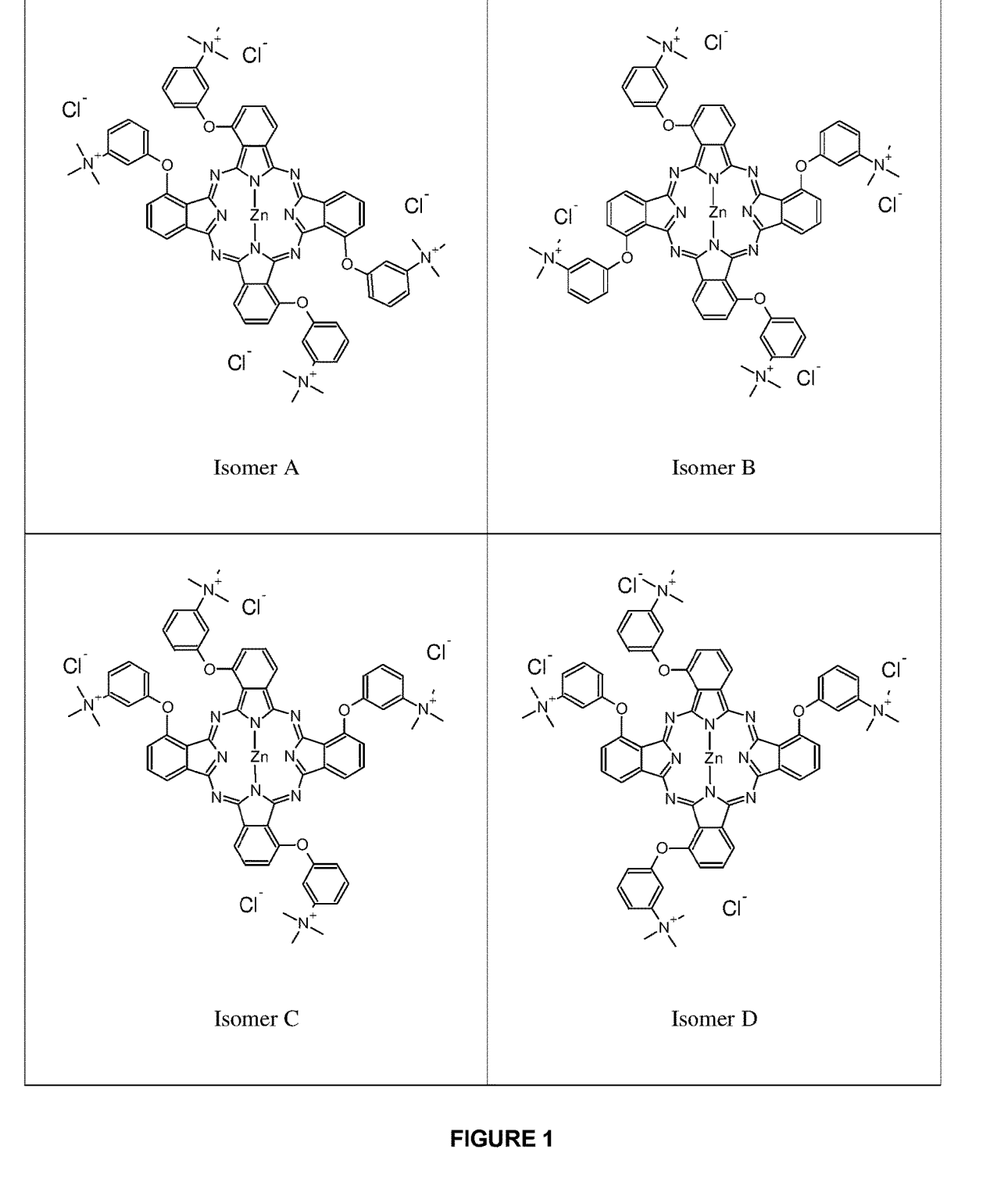
FIG. 1 shows the chemical structure of the four isomers of the compound [1,8(11),15(18),22(25)-tetrakis-(3-N,N,N-trimethylammonium phenoxy)] zinc phthalocyaninate (tetrachloride).

The compounds described and obtained according to the processes indicated in the above documents have proven to be effective photosensitising agents in PDT treatment, both for tumours and for microbial infections; in particular the product [1,8(11),15(18),22(25)-tetrakis-(3-N,N,N-trimethylammonium phenoxy)] zinc phthalocyaninate tetraiodide, corresponding to example 53 of EP 906 758, has proved to be particularly active. It is known that tetra-substituted phthalocyanine derivatives, such as the compound [1,8(11), 15(18),22(25)-tetrakis-(3-N,N,N-trimethylammonium phenoxy)] zinc phthalocyaninate tetraiodide, corresponding to example 53 of EP 906 758, are obtained as a mixture of four positional isomers (see FIG. 1), identified according to the symmetry classes ($D_{2h}$, $C_{4h}$, $C_s$, $C_{2v}$), and hereinafter respectively named with the letters of the alphabet (A, B, C, D). The aforesaid isomers are formed during the synthesis of the phthalocyanine macrocycle in relative percentages which differ from the theoretical (defined by statistics and respectively equal to 12.5%, 12.5%, 50% and 25%) as a function of the synthesis method used, the nature of the phthalonitrile substituents employed for preparation and, finally, of the central metal inserted, but which are constant, given the same compound and method (Phthalocyanines: Properties and Applications, Volume 4, Chapter 1 C. C. Leznoff and A. B. P. Lever (York University, Canada). VCH: New York, 1996).

As a result, a particular compound, prepared through a specific synthesis method, such as example 53 of EP 906 758, will have a typical and reproducible isomers distribution.

Also using the synthesis process described in the patent EP 1 883 640, through which the compound [1,8(11),15(18), 22(25)-tetrakis-(3-N,N,N-trimethylammonium phenoxy)] zinc phthalocyaninate is obtained as tetrachloride (example 4), the new salt is in any case present as a mixture of four isomers, according to the isomers distribution expected and already obtained with the process indicated in EP 906 758.

The exact isomers distribution of a particular tetra-substituted phthalocyanine derivative can be known and controlled using the separation process described in the patent EP 1 444 236.

During characterization studies of [1,8(11),15(18),22(25)-tetrakis-(3-N,N,N-trimethylammonium phenoxy)] zinc phthalocyaninate (tetraiodide or tetrachloride), the Applicant has discovered that the compound identified above, obtained by following known synthesis processes, contains related substances in a percentages greater than 0.1%, whose reduction/elimination is difficult to achieve. Even using the synthesis process described in the European Patent EP 1 883 640, and therefore preparing said compound as chloride (example 4), although obtaining an improvement in terms of solubility and product purity, it is not possible to reduce said impurities in the final product below 0.1% by weight (threshold above which structural identification and toxicological qualification is required).

Moreover the related substances described above have considerable structural similarities compared to the active substance, are able to interact with the light radiation used in PDT and, unlike all other impurities, cannot be eliminated from batches of the ammonium derivative [1,8(11),15(18), 22(25)-tetrakis-(3-N,N,N-trimethylammonium phenoxy)] zinc phthalocyaninate (tetraiodide or tetrachloride). Therefore, there is still the need of improving the purity of the compound [1,8(11),15(18),22(25)4tetrakis-(3-N,N,N-trimethylammonium phenoxy)] zinc phthalocyaninate tetrachloride, in view of its use as a drug substance.

BRIEF DESCRIPTION OF THE FIGURES

FIGS. 3 *a* and *b* respectively show the HPLC chromatograms of compound (II) and of compound (III).

FIGS. 5 *a* and *b* respectively show the chromatograms of the product of formula (VI) and of the product of formula (I).

SUMMARY OF THE INVENTION

The present invention relates to a phthalocyanine compound of formula (I) as indicated below, consisting of 4 isomers wherein the isomer B is present in a quantity equal to or less than 1% by weight.

DETAILED DESCRIPTION OF THE INVENTION

The Applicant has now surprisingly found that the unwanted related substances found in the product [1,8(11), 15(18),22(25)-tetrakis-(3-N,N,N-trimethylammonium phenoxy)] zinc phthalocyaninate (both in the form of iodide (V) and chloride (VI)) derive from impurities present that are formed during the synthetic process of the amino intermediate (II).

The Applicant has also surprisingly found that these impurities can be removed through a chromatography process of the intermediate, characterized by simultaneous significant elimination of the isomer B, one of the four positional isomers of the active substance. The Applicant, on the basis of the chromatographic affinities existing between the isomer B and the unwanted related substances, has also defined the maximum quantity of isomer B that must be present in compound (I) to have a simultaneous quantity of unwanted impurities ≤0.1% by weight. The value of the percentage of B has been found to correspond to 1% by weight.

Therefore, the subject matter of the present invention is the phthalocyanine derivative of formula (I), consisting of a mixture of 4 isomers, identified as A/B/C/D, wherein the percentage of isomer B present is ≤1% by weight.

The state of the art closest to the subject matter of the present invention is represented by the compound described in example 53 of EP 906 758. Example 53 has the same substituents on the phthalocyanine macrocycle, but nonetheless differs from (I) for two principal and mutually related characteristics:

1) the four positional isomers are present according to the distribution expected from the synthesis of the phthalocyanine nucleus, in fact after their formation, none of the obtained isomers is partially or totally removed; the unwanted impurities are present in a quantity 0.1% by weight, which makes the example 53 of EP 906 758 less adequate to be used as a drug substance. Coversely the aforesaid impurities are instead below 0.1% in the batches of product (I), obtained according to a preparation process that includes the following steps (see also FIG. 2, where the synthesis that leads to obtainment of (I) is compared with the process described in the patents EP 906 758 and EP 1 883 640, in which the chromatography step ii) is not performed):

i) Base-catalyzed tetramerisation of 3-dimethylamino phenoxy phthalonitrile and preliminary purification of the obtained amino phthalocyanine intermediate (II);

ii) Chromatographic purification of compound (II) to give the amino intermediate "with low isomer B content" (III);

iii) Methylation of the amino intermediate (III) with a suitable methylating agent to give the ammonium salt intermediate "with low isomer B content" (IV);

iv) Ion exchange of the ammonium salt intermediate (IV) to give the ammonium salt "with low isomer B content" in the form of chloride (I).

For the preparation of the desired product (I), the Applicant has discovered that the impurities of the intermediate (II), which are those that make compound (VI) unsuitable for the desired purposes, cannot be eliminated other than using further chromatography purification of this intermediate (II).

The Applicant has also surprisingly discovered that the chromatography process which allows effective separation of the unwanted impurities from the amino intermediate (II) involves a coelution with the aforesaid impurities of one of the four positional isomers (isomer B), which is thus mainly removed from the rest of the isomers mixture. The amino intermediate (III) obtained from this chromatography purification has a different isomers distribution, and is therefore a new compound with respect to compound (II), besides being efficiently purified from the impurities initially present.

Figure 2:
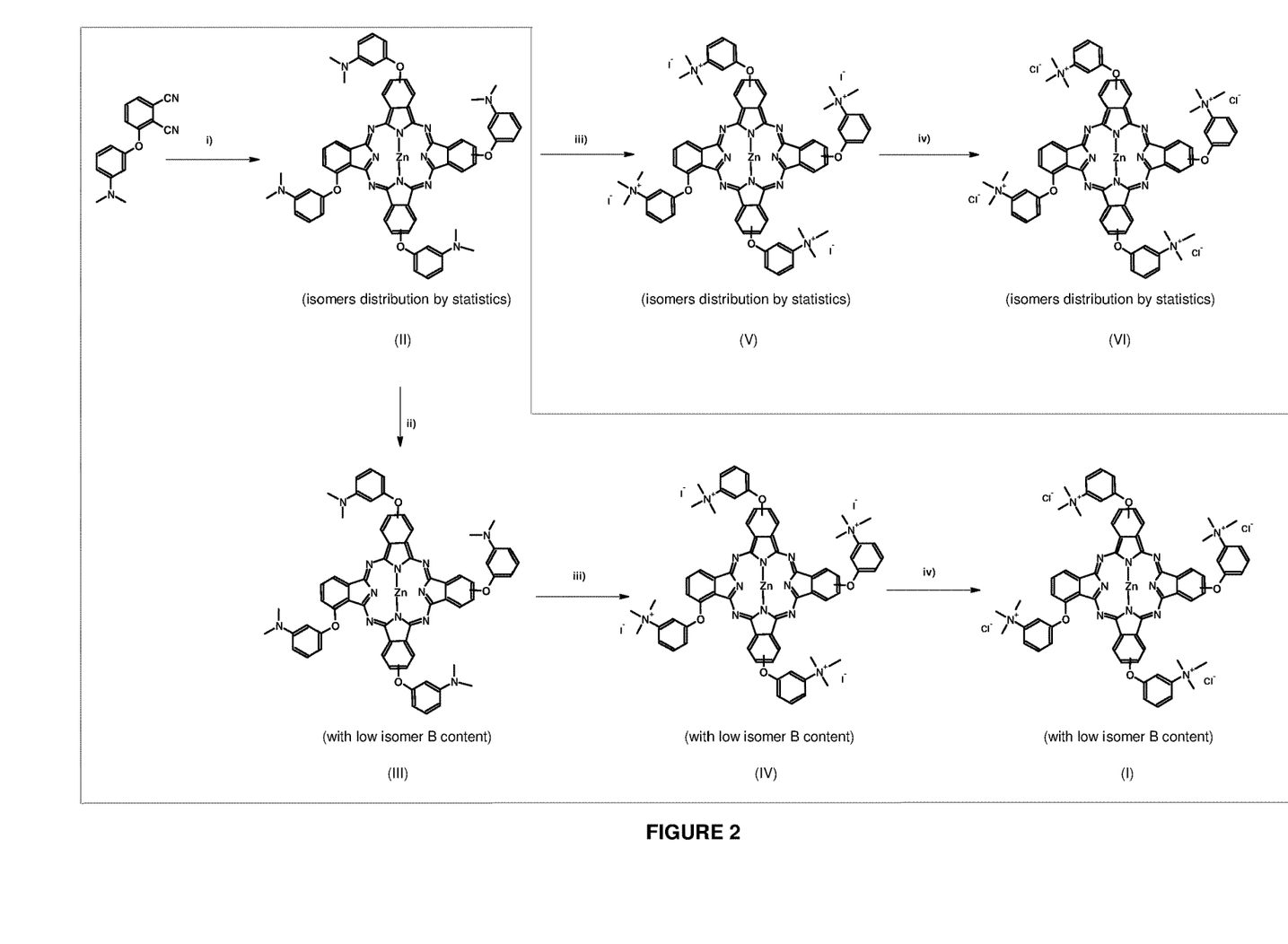
FIG. 2 shows the synthetic way to be used for the obtainment of compound of formula (I) with low isomer B content in comparison with the pathway used to obtain compound (VI), having isomers distribution by statistics.

With reference to the synthetic process described in FIG. 2, the ammonium salt (IV) obtained by methylation of the intermediate (III) has a different isomers composition from (V) and is therefore a new compound with improved purity. Likewise, the final chloride (I) obtained through ion exchange of (IV) has a different isomers distribution and is therefore a new compound with respect to (VI). Finally, compound (I) is purer than (VI).

The Applicant has also surprisingly and unexpectedly discovered that the new isomers distribution of product (I) "with low isomer B content" with respect to those indicated in patents EP 906 758 and EP 1 883 640, respectively compounds (V) and (VI), does not imply any difference in terms of pharmacological and toxicological activity.

In other words, the product thus obtained, in which the relative percentage of one of the four isomers (B) is substantially decreased, maintains the therapeutic properties of the original mixture and has improved purity, both fundamental requirements for the use of (I) as pharmaceutical active substance and therefore for the practical application of the claimed therapeutic properties. Moreover, the almost total elimination of isomer B, which occurs as a consequence of chromatographic purification, leads to a series of further advantages of compound (I), both at the level of final product and of the process intermediates, in light of the preparation and use of (I) as an active substance, advantages that are presented below, The poor solubility of the isomer B of the amino intermediate (II), due to its symmetrical structure, makes the solutions of (II) variable in terms of general isomers distribution, because incomplete dissolution and/or precipitation can occur. This takes place both during the synthesis and in the course of analytical controls, with consequent decrease of the reproducibility of the synthesis process and difficulty of validation and routine use of analytical methods, problems that are however totally inexistent for the intermediate (III).

Moreover, the low content of isomer B facilitates the characterization, by means of HPLC chromatography methods, of the product (I) (and, for the same reasons, of the last process intermediate (IV)) which results in a better control of the reproducibility of the synthesis batches.

In a preferred condition of the present invention, the content of isomer A in compound (I) is lower than 12.5% by weight.

Chromatographic purification of the amino intermediate (II), which allows removal of the unwanted impurities and the majority t of the isomer B, leading to the intermediate (III), is carried out using silica gel as stationary phase and a constant or variable mixture of organic solvents as mobile phase (elution in isocratic or gradient conditions).

For the aforesaid purification every one of the following methods can be used: Flash Chromatography (FC), Medium Pressure Liquid Chromatography (MPLC) and preparative High Pressure Liquid Chromatography (prep HPLC)

In a preferred condition, the purification is performed in FC or MPLC.

According to the selected purification method, the stationary phase can be made of irregularly shaped or spherical shape silica gel particles, with particle size in the range 5-75 μm and pore size in the range 60-150 Angstrom.

The silica gel can be packed before the cromatography run or used as pre-packed cartridges/columns.

In a preferred condition, the stationary phase is made of irregularly shaped silica gel particles, with particle size in the range 20-75 μm and pore size of 60 Angstrom.

In a particular preferred condition the stationary phase can be used for several chromatographic runs.

In a preferred condition the mobile phase is constituted by at least two organic solvents such as dichloromethane, chloroform, ethyl acetate, acetone, tetrahydrofurane, N,N-dimethylformamide, methanol, ethanol, acetonitrile, diethyl ether, pentanes, hexanes, heptanes, petroleum ether, alkylamines.

In a particularly preferred condition a constant or variable mixture of two phases X and Y is used as mobile phase.

In a particularly preferred condition X prevalently contains chlorinated solvents and Y consists of pentanes, hexanes, heptanes or petroleum ether.

In a particularly preferred condition X consists of a mixture of dichlorometane or chloroform with 0.1-10% of an agent or a mixture of agents with stronger elution power, such as tetrahydrofuran, ethyl acetate, methanol, ethanol, acetone, alkylamines.

In a particularly preferred condition X consists of a mixture 94/5/1 dichloromethane/tetrahydrofuran/methanol and Y consists of n-hexane or n-heptane.

In a preferred condition the elution is performed eluting with X/Y 3/1 in isocratic conditions.

In another preferred condition the elution is performed initially eluting with X/Y 3/1 (until elution of the isomers C and D starts) and then with X/Y 4/1 until complete elution of the isomer A.

The described chromatographic process can be applied to samples of compound (II) having different initial isomers distribution (depending both on the synthetic method and on the pre-chromatographic treatments carried out), in any case allowing the total removal of undesired related substances and lowering of isomer B content, with minimal impact on the percentages of the other three isomers.

The following examples are provided by way of non-limiting illustration of the present invention.

Example 1

Synthetic Preparation of the Compound of Formula (I)

i) Synthesis and Preliminary Purification of [1,8(11),15(18),22(25)-tetrakis-(3-N,N-dimethylamino phenoxy)] Zinc Phthalocyaninate (Compound II)

In nitrogen atmosphere, 55 g of 3-(3-N,N-dimethylamino phenoxy)phthalonitrile (0.21 moles) are solubilised in 300 ml of DMF. Subsequently 18.3 g of Zn(AcO)$_2$ (0.11 moles) and 150 ml of DBU (1 mole) are added and the reaction mixture is then heated to 130° C. and maintained at this temperature, in the dark, in nitrogen atmosphere and under vigorous stirring for 12 hours. The reaction mixture is then cooled to 0° C., treated with 1.8 l of deionised H$_2$O, and maintained under stirring at 0° C. for half an hour, the suspension is then filtered, washing the solid with H$_2$O in portions (1.3 l total) and MeOH (1×750 ml+1×180 ml).

The product is then subjected to chromatographic purification on silica gel (mobile phase: CH$_2$Cl$_2$/DMF 50/1), followed by treatment of the purified solid with ethyl ether (200 ml) for 1 hour, filtration and washing of the solid with ethyl ether (2×25 ml).

The product thus purified is solubilised in 0.5 l of CH$_2$Cl$_2$ and reprecipitated by adding 4 l of n-hexane. After filtration, washing with n-hexane (2×1 l) and drying, 60.1 g of compound (II) are obtained.

$^1$H-NMR (300 MHz, DMSO-d$_6$): δ=9.22-8.69 (m, 4H), 8.17-7.89 (m, 4H), 7.75-7.37 (m, 4H), 7.20-6.40 (m, 16H), 3.02-2.80 (m, 24H) ppm.

ESI-MS: m/z 1117, 4 [(M+H)$^+$] in positive mode

Figure 3:
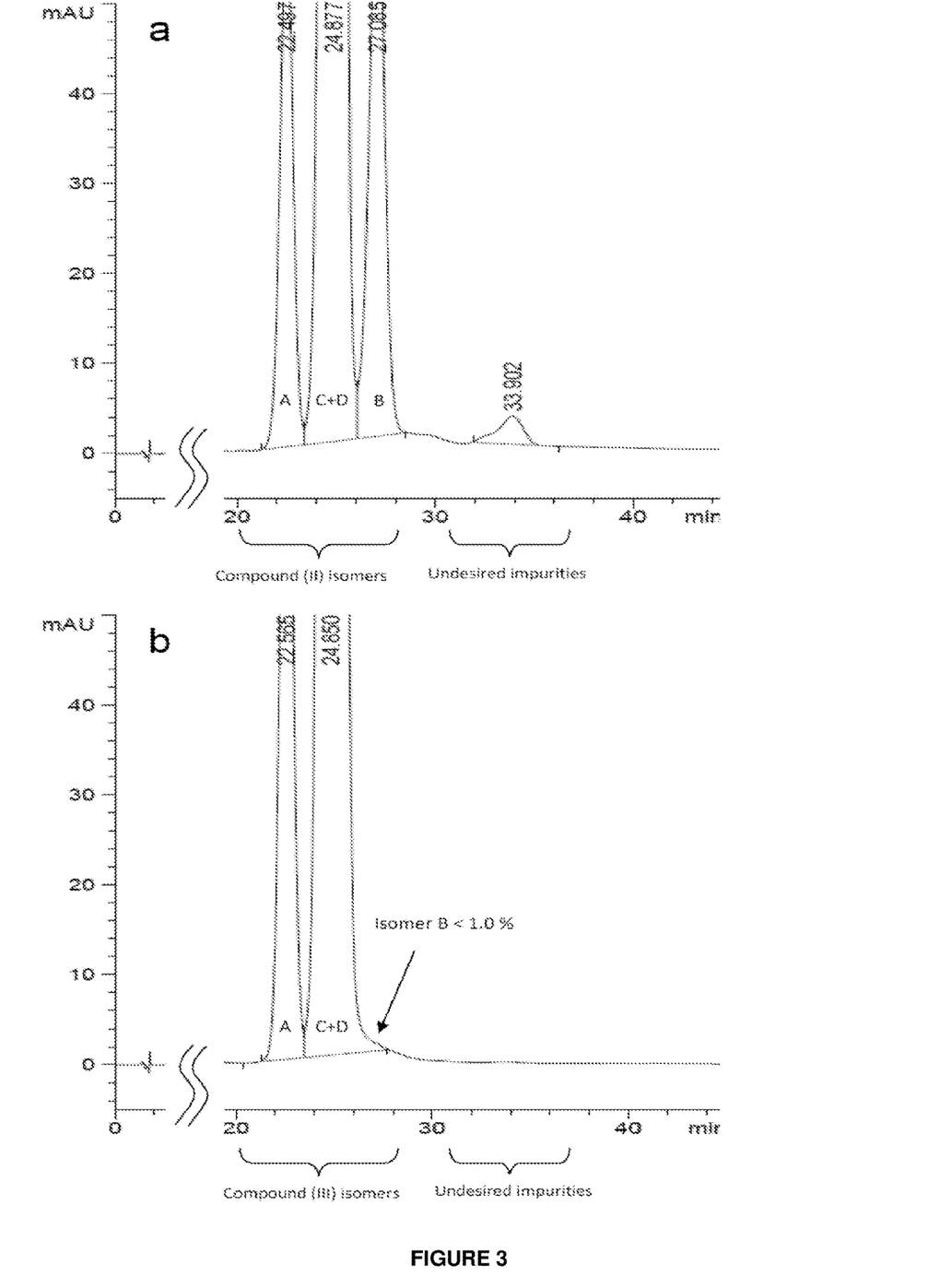

HPLC data (see FIG. 3a):

isomers distribution: B=13.9%; A=5.7%; C+D=80.4% related substances=0.8%.

ii) Chromatographic Purification of Compound (II) to Give [1,8(11),15(18),22(25)-tetrakis-(3-N,N-dimethylamion phenoxy)] Zinc Phthalocyaninate "With Low Isomer B Content" (Compound III)

25 g of [1,8(11),15(18),22(25)-tetrakis-(3-N,N-dimethylamino phenoxy)] zinc phthalocyaninate (II) are solubilised in 200 ml of an eluent mixture X/Y 3/1 where X=DCM/THF/MeOH 94/5/1 and Y=n-hexane. The solution is loaded on a chromatography column (diameter 100 mm, height 460 mm) in silica gel preconditioned with X/Y 3/1. The elution is performed at a flow of 130 ml/min by using as mobile phase X/Y 3/1, during elution of the isomer B and until initial elution of the isomers C/D, then with X/Y 4/1 during elution of the isomers C/D and A. The fractions are controlled by TLC (SiO$_2$, X/Y 4/1): all the fractions in which the isomers C+D and/or the isomer A are present are combined and concentrated to give 17.5 g of [1,8(11),15(18),22(25)-tetrakis-(3-N,N-dimethylamino phenoxy)] zinc phthalocyaninate "with low isomer B content" (III).

$^1$H-NMR (300 MHz, DMSO-d$_6$): δ=9.19-8.68 (m, 4H), 8.16-7.90 (m, 4H), 7.74-7.40 (m, 4H), 7.20-6.49 (m, 16H), 3.02-2.80 (m, 24H) ppm.

ESI-MS: m/z 1117, 4 [(M+H)$^+$] in positive mode

HPLC Data (see FIG. 3b):

isomers distribution: B≤0.1%; A=6.1%; C+D=93.9% related substances 0.1%.

iii) Synthesis of [1,8(11),15(18),22(25)-tetrakis-(3-N,N,N-trimethylammonium phenoxy)] Zinc Phthalocyaninate tetraiodide "With Low Isomer B Content" (Compound IV)

34 g (0.03 moles) of [1,8(11),15(18),22(25)-tetrakis-(3-N,N-dimethylamino phenoxy)] zinc phthalocyaninate obtained as described above at point ii) are solubilised in 850 ml of NMP, to the solution 85 ml (1.4 moles) of MeI are then added and the reaction mixture is maintained in the dark, under stirring, in nitrogen atmosphere, at ambient temperature for 96 hours.

The reaction mixture is diluted with 1.7 l of MeOH, then treated with 6.8 l of ethyl ether, obtaining a suspension that is left under stirring for half an hour and to rest for 1 hour, then filtered; the solid is washed with ethyl ether (2×0.5 l), obtaining 60 g of damp product (incalculable yield) which was found to be [1,8(11),15(18),22(25)-tetrakis-(3-N,N,N-trimethylammonium phenoxy)] zinc phthalocyaninate tetraiodide "with low isomer B content" (IV), characterized by mass spectrometry and NMR.

$^1$H-NMR (300 MHz, DMSO-d$_6$): δ=9.49-7.20 (m, 28H), 3.79-3.58 (m, 36H) ppm.

ESI-MS: m/z 294, 1 [(M−41)$^{4+}$] in positive mode.

iv) Treatment With Ion Exchange Resin That Leads to the Obtainment of [1.8(11),15(18),22(25)-tetrakis-(3-N,N,N-trimethylammonium phenoxy)] Zinc Phthalocyaninate Tetrachloride "With Low Isomer B Content" (Compound I)

60 g of compound (IV) are solubilised in 5.5 l of MeOH, and the solution is passed through a chromatographic column, having as stationary phase 500 g of Amberlite® IRA 400 (Cl) resin, previously washed with HCl 0.5 M acidic aqueous solution and conditioned with MeOH. To the eluate (approximately 6 l), maintained under stirring, ethyl ether (24 l) is slowly added, the suspension obtained is left to rest for an hour and then filtered. The solid is washed with ethyl ether (2×250 ml) and dried on the filter for about one hour to give 36 g of compound (I) $^1$H-NMR (300 MHz, DMSO-$d_6$): δ=9.45-7.23 (m, 28H), 3.77-3.58 (m, 36H) ppm.

$^{13}$CNMR (75 MHz, DMSO-$d_6$): δ=160.5, 160.4, 160.3, 157.9, 154.4, 154.1, 153.9, 153.5, 153.2, 153.1, 153.0, 152.7, 152.5, 151.9, 150.6, 150.5, 150.2, 149.6, 149.5, 149.1, 142.0, 141.9, 141.8, 132.1, 131.3, 129.4, 129.3, 129.1, 127.7, 127.5, 123.0, 122.8, 122.7, 120.7, 120.4, 118.6, 118.2, 118.0, 117.6, 116.5, 114.7, 113.4, 111.0, 57.3, 57.2 ppm.

UV-vis (DMF) $\lambda_{max}$(%): 690(100), 621(16), 391(17), 327(17).

UV-vis (H$_2$O) $\lambda_{max}$(%): 691(100), 643(49), 331(45).

ESI-MS: m/z 294, 1 [(M−4Cl)$^{4+}$] in positive mode

HRMS: m/z 294, 1114 [(M−4Cl)$^{4+}$] in positive mode. A Δ=1.08 ppm from the theoretical mass of $C_{68}H_{64}N_{12}O_4Zn$ Isomers distribution: A=6.5% B<0.2%, C=62.0%, D=31.5%.

Example 2

Starting From a Batch of Compound (II) With the Following Isomers Distribution:
A=8.6%, B=4.0% C+D=87.4%;

Performing the Chromatography Purification (Step ii)) as Described:
28.6 g of [1,8(11),15(18),22(25)-tetrakis-(3-N,N-dimethylaminophenoxy)] zinc phthalocyaninate (II) are dissolved in 192 ml of an eluent mixture X/Y 3/1 in which X=DCM/THF/MeOH 94/5/1 e Y=n-hexane. The sample is loaded on a chromatographic column (d=100 mm, h=460 mm) packed with silica gel Davisil 60 (40-63 μm) conditioned with X/Y 3/1. The elution (Flow: 130 ml/min), is performed with X/Y 3/1 until all isomer B is eluted, then ratio of the mixture X/Y is carried to 4/1 and so kept for the elution of isomers C, D and A. The selected fractions are collected and dried to give 23.2 g of [1,8(11),15(18),22(25)-tetrakis-(3-N,N-dimethylaminophenoxy)] zinc phthalocyaninate "with low isomer B content" (III) with the following isomers distribution are obtained: A=7.8%, B=0.3% C+D=91.9%;

Performing Steps iii) and iv) on This Batch of Compound (III):
a batch of compound (I) with the following isomers distribution is obtained: A=8.2%, B=0.4%, C=65.5%, D=25.9%.

Example 3

Starting From a Batch of Compound (III) With the Following Isomers Distribution:
A=7.9%, B=9.9% C+D=82.2%;

Performing the Chromatography Purification (Step ii)) as Described:
40.0 g of [1,8(11),15(18),22(25)-tetrakis-(3-N,N-dimethylaminophenoxy)] zinc phthalocyaninate (II) are dissolved in 192 ml of an eluent mixture X/Y 3/1 in which X=DCM/THF/MeOH 94/5/1 e Y=n-hexane. The sample is loaded on a chromatographic column (d=100 mm, h=460 mm) packed with silica gel Davisil 60 (20-45 μm) conditioned with X/Y 3/1. The elution (Row: 130 ml/min) is performed with X/Y 3/1 until all isomer B is eluted, then ratio of the mixture X/Y is carried to 4/1 and so kept for the elution of isomers C, D and A. The selected fractions are collected and dried to give 30.1 g of [1,8(11),15(18),22(25)-tetrakis-(3-N,N-dimethylaminophenoxy)] zinc phthalocyaninate "with low isomer B content" (III) with the following isomers distribution are obtained: A=7.5%, B=0.3% C+D=92.2%;

Performing Steps iii) and iv) on This Batch of Compound (III):
a batch of compound (I) with the following isomers distribution is obtained: A=7.8%, B=0.3%, C=64.9%, D=27.0%.

Example 4

Starting From a Batch of Compound (II) With the Following Isomers Distribution:
A=7.7%, B=4.4% C+D=87.9%;

Performing the Chromatography Purification (Step ii)) as Described:
49.6 g of [1,8(11),15(18),22(25)-tetrakis-(3-N,N-dimethylaminophenoxy)] zinc phthalocyaninate (II) are dissolved in 235 ml of an eluent mixture X/Y 3/1 in which X=DCM/THF/MeOH 94/5/1 e Y=n-hexane. The sample is loaded on a chromatographic column (d=100 mm, h=460 mm) packed with silica gel Davisil 60 (20-45 μm) conditioned with X/Y 3/1. The elution (Flow: 130 ml/min) is performed with X/Y 3/1 until all isomer B is eluted, then ratio of the mixture X/Y is carried to 4/1 and so kept for the elution of isomers C, D and A. The selected fractions are collected and dried to give 38.2 g of [1,8(11),15(18),22(25)-tetrakis-(3-N,N-dimethylaminophenoxy)] zinc phthalocyaninate "with low isomer B content" (III) with the following isomers distribution are obtained: A=7.6%, B=0.9% C+D=91.5%;

Performing Steps iii) and iv) on This Batch of Compound (III):
a batch of compound (I) with the following isomers distribution is obtained: A=5.6%, B=0.9%, C=61.4%, D=32.1%.

Example 5

Starting From a Batch of Compound (II) With the Following Isomers Distribution:
A=7.0%, B=4.6% C+D=88.4%;

Performing the Chromatography Purification (Step ii)) as Described:
32.0 g of [1,8(11),15(18),22(25)-tetrakis-(3-N,N-dimethylaminophenoxy)] zinc phthalocyaninate (II) are dissolved in 288 ml of dichloromethane. The sample is loaded on a chromatographic column (d=100 mm, h=460 mm) packed with silica gel Davisil 60 (40-63 μm) and conditioned with X/Y 3/1. The elution (Flow: 130 ml/min) is performed in isocratic mode with mobile phase X/Y 3/1 The selected fractions are collected and dried to give 30.1 g of [1,8(11),15(18),22(25)-tetrakis-(3-N,N-dimethylaminophenoxy)] zinc phthalocyaninate "with low isomer B content" (III) with the following isomers distribution are obtained: A=6.2%, B<0.1% C+D=93.8%;

Performing Steps iii) and iv) on This Batch of Compound (III):
a batch of compound (I) with the following isomers distribution is obtained: A=6.4%, B=0.2%, C=55.8%, D=37.6%.

Example 6

Starting From a Batch of Compound (II) With the Following Isomers Distribution:
A=6.9%, B=7.8% C+D=85.3%;

Performing Three Chromatography Purifications (Step ii) a, b, c) on the Same Stationary Phase, as Described:
a) 17.6 g of [1,8(11),15(18),22(25)-tetrakis-(3-N,N-dimethylaminophenoxy)] zinc phthalocyaninate (II) are dissolved in 256 ml of dichloromethane. The sample is loaded on a chromatographic column (d=100 mm, h=460 mm) packed with silica gel Davisil 60 (40-63 µm) conditioned with X/Y 3/1. The elution (Flow: 130 ml/min) is performed in isocratic mode with mobile phase X/Y 3/1 The selected fractions are collected and dried to give 13.1 g of [1,8(11), 15(18),22(25)-tetrakis-(3-N,N-dimethylaminophenoxy)] zinc phthalocyaninate with "low isomer B content" (III) with the following isomers distribution are obtained: A=5.1%, B<0.2% C+D=94.9%;

b) After a washing of the column with 16 l of mobile phase X/Y 3/1, the second run is performed: 14.4 g of [1,8(11),15(18),22(25)-tetrakis-(3-N,N-dimethylaminophenoxy)] zinc phthalocyaninate (II) are dissolved in 256 ml of dichloromethane. The sample is loaded on a chromatographic column (d=100 mm, h=460 mm) packed with silica gel Davisil 60 (40-63 µm) and conditioned with X/Y 3/1. The elution (Flow: 130 ml/min) is performed in isocratic mode with mobile phase X/Y 3/1 The selected fractions are collected and dried to give 10.2 g of [1,8(11),15(18),22(25)-tetrakis-(3-N,N-dimethylaminophenoxy)] zinc phthalocyaninate "with low isomer B content" (III) with the following isomers distribution are obtained: A=3.5%, B=0.5% C+D=96.0%;

c) After a washing of the column with 16 l of mobile phase X/Y 3/1, the third run is performed: 11.2 g of [1,8(11),15 (18),22(25)-tetrakis-(3-N,N-dimethylaminophenoxy)] zinc phthalocyaninate (II) are dissolved in 256 ml of dichloromethane. The sample is loaded on a chromatographic column (d=100 mm, h=460 mm) packed with silica gel Davisil 60 (40-63 µm) and conditioned with X/Y 3/1. The elution (Flow: 130 ml/min) is performed in isocratic mode with mobile phase X/Y 3/1 The selected fractions are collected and dried to give 7.9 g of [1,8(11),15(18),22(25)-tetrakis-(3-N,N-dimethylaminophenoxy)] zinc phthalocyaninate "with low isomer B content" (III) with the following isomers distribution are obtained: A=3.5%, B=0.5% C+D=96.0%;

Performing Steps iii) and iv) on the Batches of Compound (III) Obtained From Step ii a, b, c three batches compound (I) with the following isomers distribution are obtained:

a) A=4.8%, B<0.2%, C=56.9%, D=38.2%;
b) A=3.2%, B=0.4%, C=57.2%, D=39.2%;
c) A=3.3%, B=0.5%, C=56.8%, D=39.4%.

Example 7

Starting From a Batch of Compound (II) With the Following Isomers Distribution:

A=6.7%, B=6.5%, C+D=86.8%;

Performing the Chromatography Purification (Step ii)) as Described:

1.8 g of [1,8(11),15(18),22(25)-tetrakis-(3-N,N-dimethylaminophenoxy)] zinc phthalocyaninate (II) are dissolved in 12 ml of an eluent mixture X/Y 3/1 in which X=DCM/THF/MeOH 94/5/1 e Y=n-hexane. The sample is loaded on a chromatographic pre-packed column (Biotage SNAP KP-Sil Cartridge, silica gel 100 g, mesh 40-63 µm) pre-conditioned with X/Y 3/1. The elution (Flow: 40 ml/min) is performed with X/Y 3/1 until ail isomer B is eluted, then ratio of the mixture X/Y is carried to 4/1 and so kept for the elution of isomers C, D and A. The selected fractions are collected and dried to give 1.4 g of [1,8(11),15(18),22(25)-tetrakis-(3-N,N-dimethylaminophenoxy)] zinc phthalocyaninate "with low isomer B content" (III) with the following isomers distribution are obtained: A=7.4%, B=0.4%, C+D=92.2%;

Performing Steps iii) and iv) on This Batch of Compound (III):

a batch of compound (I) with the following isomers distribution is obtained: A=7.6%, B=0.5%, C=62.6%, D=29.3%.

Example 8

Experimental Proof of the Difficulty of Preparing Solutions of (II), Due to the Low Solubility of the Isomer B.

Figure 4:
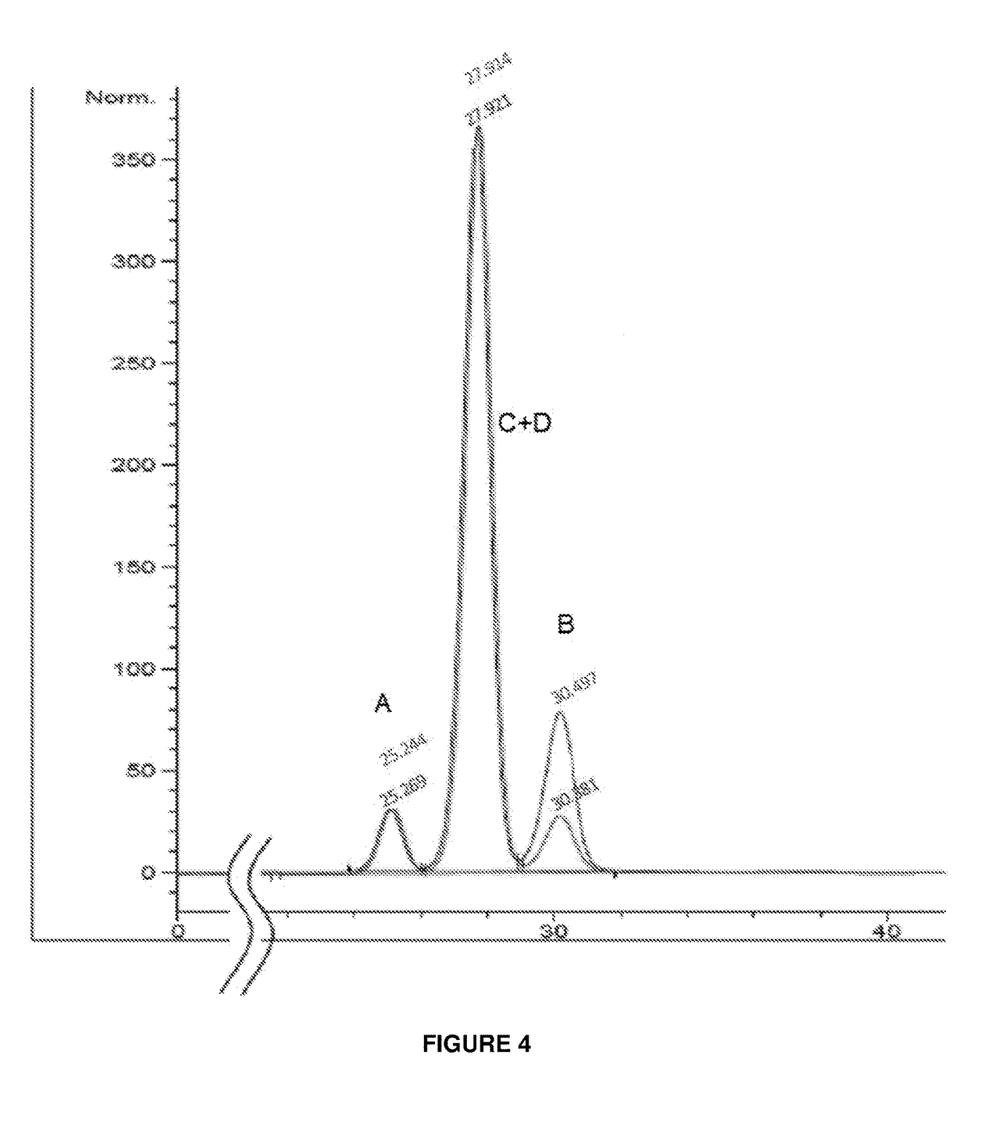
FIG. 4 shows the superimposed HPLC chromatograms o compound (II) after solubilisation in DMF and in THF/MeOH mixture (1:1).

Two samples of the same batch of intermediate (II) are solubilised (2 mg/ml) in, DMF and THF/MeOH 1/1. The solutions are appropriately diluted and analysed in HPLC. As shown in Table 1, and in FIG. 4, the two samples have a different percentage of isomer B, which is much lower in the sample coming from the solution in THF/MeOH 1/1, This is due to the precipitation of isomer B from the THF/MeOH 1/1 solution, as a consequence of the lower solubility of the isomer B in comparison to the other isomers. This behaviour can lead to the preparation of samples having variable composition and, ultimately, to the production of not reliable analytical data including the ones concerning the other isomers

TABLE 1

HPLC analysis of the isomer distribution of two samples of the same batch of compound (II)

| % isomers | Compound (II) from stock solution 2 mg/ml in DMF An. N.. 0315/09 | Compound (II) from stock solution 2 mg/ml in THF/MeOH (1:1) An. N. 0315/09 |
| --- | --- | --- |
| % A | A: 5.9% | A: 6.7% |
| % C + D | C + D: 79.2% | C + D: 86.7% |
| % B | B: 14.9% | B: 6.6% |

Example 9

Demonstration of Non Resolution Between the HPLC Peaks of t Isomers B and C of compound (VI)

Figure 5:
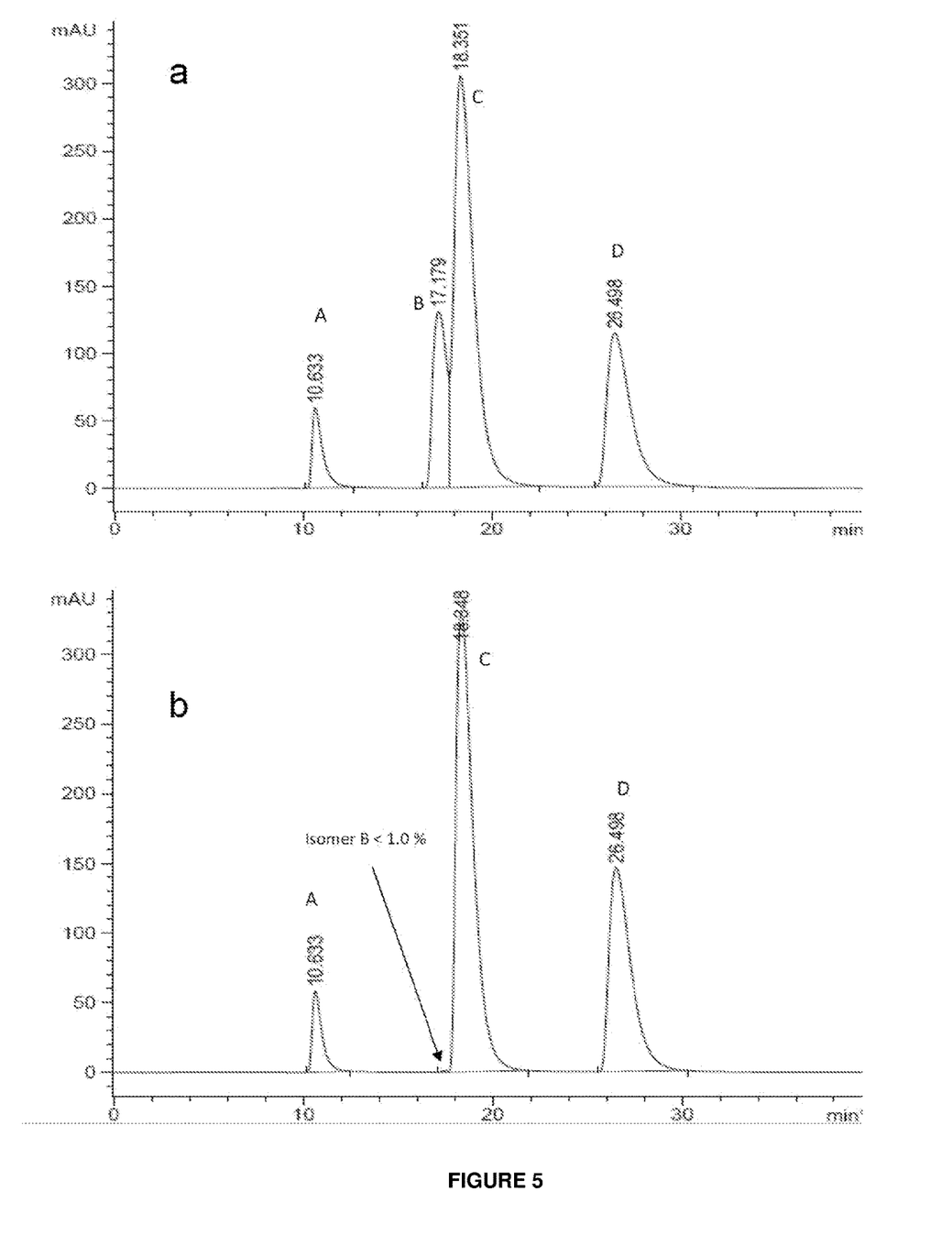

FIG. 5 compares the HPLC chromatograms relative to the isomers distribution of a sample of compound (VI) (5a) and of a sample of compound (I) (5b). It is evident that the resolution between the peaks relative to the isomers B and C is not complete; when the presence of isomer B is beyond 1%, a non-negligible error is introduced in the quantification of the isomers abundances, making the method described unsuitable for the characterization of batches of a drug substance. Conversely the problem is non-existent if a batch of compound (I) is analysed, as the very small quantity of isomer B generates a negligible estimation error of the isomers A, C and D ratio.

The compound of formula (I), prepared as described, can be used as a drug substance in the preparation of pharmaceutical compositions, included those intended to be used for photodynamic therapy, comprising, in combination with the aforesaid drug substance, pharmaceutically acceptable excipients and/or diluents. These pharmaceutical compositions can be intended to be used for both systemic and topical administration to humans and animals and can be in solution, suspension, cream, ointment, gel or spray form. Controlled release administration of the composition is also possible. These pharmaceutical compositions can also contain a metal chelating agent, with preference for metal chelating agents having specificity for the ions $Ca^{2+}$ and $Mg^{2+}$.

In a particularly preferred condition, said metal chelating agent is selected in the group consisting of ethylenediamine-N,N,N',N'-tetraacetic acid (EDTA), 1,2-diaminocyclohexane-N,N,N',N'-tetraacetic acid (CDTA) and diethylene triamine pentaacetic acid (DTPA).

Due to the non specific (multi-target) mechanism of action, the aforesaid pharmaceutical compositions, containing the phthalocyanine derivative of formula (I) can be intended to be used for photodynamic treatment of various pathologies (microbial infections, hyperproliferative diseases, psoriasis, actinic keratosis and pre-tumour or tumour pathologies). In a particularly preferred condition, the pharmaceutical compositions containing the phthalocyanine derivative of formula (I) are intended to be used for the preventive or curative photodynamic treatment of microbial infections.

Finally, the derivative of formula (I) can also be used as component of medical devices, in particular in the disinfection of wounds, as sterilisation agent, also ex vivo, and as in vivo diagnostic agent.

The invention claimed is:

1. An isomeric mixture of a phthalocyanine derivative of formula (I)

(I)

wherein said isomeric mixture consists of:

Isomer A

,

Isomer B

,

Isomer C and

-continued

Isomer D wherein isomer B is present in the mixture at ≤1% by weight and non-isomeric impurities are present in the mixture at a level of <0.1% by weight.

2. The isomeric mixture of claim 1 wherein the isomer B is present in the mixture at <0.2% by weight and isomer A is present in the mixture at <12.5% by weight.

3. The isomeric mixture of claim 2 wherein the isomers A/C/D are present in the mixture in the following relative contents: 5.5-7.0% (A), 56.0-63.5% (C), and 30.0-38.0% (D).

4. A pharmaceutical composition comprising the isomeric mixture of claim 2 in combination with a pharmaceutically acceptable excipient diluent or chelating agent.

* * * * *